United States Patent [19]

Berthe et al.

[11] Patent Number: 5,315,045

[45] Date of Patent: May 24, 1994

[54] MANUFACTURE OF FLUOROETHYLENES AND CHLOROFLUOROETHYLENES

[75] Inventors: Bernard Berthe, Marseille; Jean-Marie Cognion, Saint-Genis-Laval, both of France

[73] Assignee: Elf Atochem S.A., France

[21] Appl. No.: 788,388

[22] Filed: Nov. 6, 1991

[30] Foreign Application Priority Data

Nov. 6, 1990 [FR] France .................. 90 13705

[51] Int. Cl.$^5$ .................. C07C 17/02; C07C 17/34
[52] U.S. Cl. .................. 570/153; 570/156
[58] Field of Search .................. 570/153, 156

[56] References Cited

U.S. PATENT DOCUMENTS

| | | | |
|---|---|---|---|
| 2,697,124 | 12/1954 | Mantell | 570/156 |
| 2,802,887 | 8/1957 | Miller | 570/156 |
| 3,564,064 | 2/1971 | Nakagawa | 570/156 |
| 4,876,405 | 10/1989 | Gervasutti | |

FOREIGN PATENT DOCUMENTS

| | | | |
|---|---|---|---|
| 655397 | 1/1963 | Canada | 570/156 |
| 053657 | 9/1981 | European Pat. Off. | |
| 0253410 | 1/1988 | European Pat. Off. | 570/156 |
| 459463 | 12/1991 | European Pat. Off. | |
| 698386 | 10/1953 | United Kingdom | 570/156 |

OTHER PUBLICATIONS

Bi-Pd Catalyst for Selective Hydrodechlorination of 1,1,2-Trichlorotrifluoroethane to Trifluoroethene, a Key Intermediate to 1,1,1,2-Tetrafluoroethane as a CFC Replacement for Refrigeration, Ohnishi, et al., The Chemical Society of Japan, Chemistry Letters, pp. 841–844, 1991.

*Primary Examiner*—Alan Siegel
*Attorney, Agent, or Firm*—Morgan & Finnegan

[57] ABSTRACT

The invention relates to hydrogenolysis of a chlorofluoroethane XYClC—CClX'Y' or of a chlorofluoroethylene XClC=CX'Y (where at least one of the symbols X, X', Y and Y' is a fluorine atom and the others are hydrogen or chlorine atoms) which is performed on a mixed catalyst based on copper or silver and on at least one platinum group metal (Ru, Rh, Pd, Os, Ir, Pt), these metals being deposited on a support.

Even at low operating temperatures, excellent degrees of conversion and selectivities for fluoroethylenes and/or chlorofluoroethylenes are obtained.

9 Claims, No Drawings

MANUFACTURE OF FLUOROETHYLENES AND CHLOROFLUOROETHYLENES

FIELD OF THE INVENTION

The present invention relates to the preparation of fluoroethylenes and chlorofluoroethylenes by catalytic hydrogenolysis of chlorofluoroethanes or of chlorofluoroethylenes.

BACKGROUND OF THE INVENTION

The hydrogenolysis of chlorofluoroethanes is a reaction which has been known for a long time (Patent GB 698,386), and many improvements have been made to it. There may be mentioned, for example, Patent GB 931,643, which employs a chromium oxide catalyst on an alumina support for the hydrogenolysis of 1,1,2-trichloro-1,2,2-trifluoroethane (F113) at temperatures in the region of 500° C., and U.S. Pat. No. 3,636,173, which recommends for the hydrogenolysis of fluorohalocarbons a catalyst based on nickel or chromium on an alumina support activated beforehand with hydrofluoric acid. However, the catalytic compositions described in these patents necessitate high operating temperatures (from 300° to 600° C.) and the degrees of conversion or selectivities are low.

More recently, Patent EP 53,657 describes a process for the dehydrochlorination of F113 to chlorotrifluoroethylene (F1113) and trifluoroethylene (F1123) by means of a catalyst comprising a platinum group metal deposited on an alkaline magnesium fluoride type support. The results show a rapid deactivation of this catalyst with a substantial formation of 1,1,2-trifluoroethane (F143) and 1-chloro-1,2,2-trifluoroethane (F133) as by-products, even with low degrees of conversion of F113.

In Patent EP 355,907, a catalyst is described comprising an oxygenated porous support impregnated with a group VIII metal and a salt of an alkali metal or alkaline earth metal. The examples given show degrees of conversion of F113 of the order of 50% and selectivities for F1113 and F1123 which do not exceed 80%.

It is known, moreover, that catalysts based on copper alone are active in the hydrogenolysis of chlorofluoroalkanes. In U.S. Pat. No. 2,615,925, which employs such a catalyst, the operating temperatures are high (above 500° C.) and the degrees of conversion and yields are mediocre.

It is also known that catalysts based on palladium are active. However, U.S. Pat. No. 4,876,405 shows that the use of such a catalyst in the hydrogenolysis of symmetrical difluorotetrachloroethane (F112) and of F113 leads to a substantial formation (more than 10%) of saturated by-products such as 1,1-difluoroethane (F152a) and 1,1,2-trifluoroethane (F143).

Moreover, the use of mixed catalysts has already been proposed. There may be mentioned U.S. Pat. No. 2,864,873 relating to mixed catalysts based on copper and on nickel on a chromium oxide support. These catalysts, which function at temperatures from 325° to 425° C., lead to degrees of conversion of F113 to F1113 of less than 50%. U.S. Pat. No. 2,697,124 relating to a copper/cobalt mixed catalyst on a magnesium fluoride support may also be mentioned; despite high temperatures (above 400° C.) for the hydrogenolysis of F113, this catalyst gives degrees of conversion of F113 of less than 80%. The hydrogenolysis of F113 and of F114 with mixed catalysts based on copper and on chromium is also described in Patents BE 653,362 and FR 1,409,109; the operating temperatures are high, and the degrees of conversion and the yields of ethylenic compounds are low. The same applies to U.S. Pat. No. 3,505,417, which describes the hydrogenolysis of F114 to tetrafluoroethylene on copper/chromium or copper/cobalt catalysts.

It has now been found that, for the hydrogenolysis of chlorofluoroethanes or of chlorofluoroethylenes, the use of mixed catalysts based on copper or silver and on at least one platinum group metal (ruthenium, rhodium, palladium, osmium, iridium or platinum) enables excellent degrees of conversion and selectivities to be obtained at low operating temperatures.

DESCRIPTION OF THE INVENTION

The subject of the invention is hence a process for the manufacture of fluoroethylenes and/or chlorofluoroethylenes by catalytic hydrogenolysis of a chlorofluoroethane of general formula:

in which at least one of the symbols X, X', Y and Y' represents a fluorine atom and the others, which may be identical or different, each represent a hydrogen or chlorine atom, or of a chlorofluoroethylene of general formula:

in which at least one of the symbols X, X' and Y represents a fluorine atom and the others, which may be identical or different, each represent a hydrogen or chlorine atom, characterised in that a mixed catalyst based on copper or silver and on at least one platinum group metal, preferably palladium, is used, these metals being deposited on a support.

In the mixed catalyst according to the present invention, the copper and/or silver content can range from 1 to 20% by weight, and preferably between 3 and 15%, and that of the platinum group metal can range from 0.1 to 10% by weight. The degree of conversion of the chlorofluoroethane (I) or of the chlorofluoroethylene (II) varies positively with the content of the platinum group metal; however, to avoid the concomitant formation of fluoroethanes, it is preferable to employ a catalyst containing from 0.1 to 5% of the said metal.

Although it is preferable to use an active charcoal as a support, it is possible to employ other well-known supports such as, for example, $Al_2O_3$ and $AlF_3$. The support can take various forms such as, for example, extruded, pelleted, ground or bead forms.

The preparation of the mixed catalyst according to the invention is very simple, and may be carried out in various ways, either by coimpregnation of the support with copper or silver and at least one platinum group metal, or by successive impregnation with the different metals.

The impregnation of the support may be performed, for example, by immersion or spraying by means of a solution of salts of the metals to be deposited. This operation may be conducted at a temperature ranging from approximately 20° to 80° C., but is preferably carried out at room temperature. The solvent, which is preferably water but can also be a hydrocarbon, a light alcohol or a ketone, is then evaporated off under vacuum while the temperature is gradually raised. Before use, the catalyst is reduced under a stream of hydrogen (10 to 80 l/h per 100 g of catalyst) at a temperature of between 100° and 500° C.

As metal salts for the impregnation, chlorides are advantageously used. However, other salts (for example nitrates, acetates, acetylacetonates) may be employed; the only important factor is that these salts are sufficiently soluble in the solvent to obtain the desired weight concentrations of the metals.

Another method of preparing a catalyst according to the invention consists in starting with a commercial supported catalyst based on a platinum group metal and impregnating it with a solution of a copper or silver salt, the evaporation of the solvent and the final reduction being carried out in the same manner as in the case of coimpregnation.

The catalyst according to the invention may be employed according to any technique of hydrogenolysis, such as, in particular, those employing fixed-bed or fluidized-bed operation.

The hydrogenolyis process according to the invention involves one and/or other of the following reactions:

XYClC—CClX'Y' + H$_2$ ⟶ XYC=CX'Y' + 2HCl

XClC=CX'Y + H$_2$ ⟶ XHC=CX'Y + HCl

As non-limiting examples of chlorofluoroethanes (I) and of chlorofluoroethylenes (II) which may be hydrogenalized according to the present process, there may be mentioned, more especially, 1,2-difluoro-1,1,2,2-tetrachloroethane (F112), 1,1,2-trichloro-1,2,2-trifluoroethane (F113), 1,2-dichloro-1,1,2,2-tetrafluoroethane (F114), 1,2-dichloro-1,1,2-trifluoroethane (F123a), 1,2-dichloro-1,1-difluoroethane (F132b) and chlorotrifluoroethylene (F1113).

The hydrogenolysis may be performed at a temperature ranging from 100° to 400° C., and preferably between 150° and 350° C. The reaction is advantageously performed at atmosphere pressure, but working at a pressure below or above atmospheric pressure will not constitute a departure from the scope of the present invention.

The mole ratio of hydrogen to the chlorofluoroethane (I) or chlorofluoroethylene (II) is generally between 0.1 and 10, and preferably between 0.5 and 5.

The contact time can vary between 1 and 45 seconds, but excellent results have been obtained with contact times of between 2 and 10 seconds.

EXAMPLES

The examples which follow illustrate the invention without limiting it.

EXAMPLE 1

A—Preparation of the Catalyst 150 g of an aqueous cupric chloride solution containing 15 g of copper are added in a rotary evaporator at 20° C. to 150 g of a commercial catalyst in extrudate form containing 0.8% of palladium on active charcoal, possessing a BET surface area of more than 500 m$^2$/g and having a metal surface area of more than 100 m$^2$/g of palladium. The water is then evaporated off under vacuum While the temperature is gradually raised to 170° C. The catalyst is then reduced at 170° C. for 8 hours under a stream of hydrogen (25 liters/hour at atmospheric pressure).

A catalyst is thereby obtained, ready for use, containing 0.7% of palladium and 9% of copper.

B—Hydrogenolysis of F113

1.26 ml of the catalyst described above are introduced into an electrically heated stainless steel 316 L tube 4 mm in internal diameter, and a mixture of hydrogen and F113 is then passed through at atmospheric pressure and at the temperatures, mole ratios and flow rates shown in the following table, the last three columns of which collate the results obtained.

| Reactor temp. (°C.) | Mole ratio H$_2$/F113 | Total flow rate (mole/ hour) | Degree of conversion of F113 (%) | Selectivity for: | |
|---|---|---|---|---|---|
| | | | | F1113 | F1123 |
| 250 | 3.4 | 0.045 | 98 | 81 | 16 |
| 300 | 3.4 | 0.045 | 100 | 69 | 29 |
| 320 | 5 | 0.15 | 100 | 76 | 23 |
| 320 | 4.6 | 0.045 | 100 | 55 | 42 |

EXAMPLE 2

A—Preparation of the Catalyst

A rotary evaporator is charged with 23 g of a CECA active charcoal in the form of extrudates 1.8 mm in diameter, having a porosity of 0.6 cm$^3$/g and a specific surface area of 950 m$^2$/g. 70 ml of an aqueous solution containing 2.96 g of palladium chloride and 2.7 g of hydrated cupric chloride (CuCl$_2$.2H$_2$O) are introduced, the water is then evaporated off under reduced pressure (1 kPa) and the residue is dried at 100° C. The latter is then treated at 450° C. for 3 hours under a stream of hydrogen (10 l/h), and a catalyst is thereby obtained, ready for use, containing 7% of palladium and 4% of copper.

B—Hydrogenolysis of F113

Using the procedure described in Example 1B, but with 1.26 ml of this catalyst containing 7% of palladium and 4% of copper, the results collated in the following table were obtained:

| Reactor temp. (°C.) | Mole ratio H$_2$/F113 | Total flow rate (mole/ hour) | Degree of conversion of F113 (%) | Selectivity for: | |
|---|---|---|---|---|---|
| | | | | F1113 | F1123 |
| 150 | 4 | 0.03 | 85 | 60 | 20 |
| 200 | 4 | 0.033 | 100 | 75 | 20 |
| 200 | 3 | 0.04 | 100 | 85 | 10 |
| 200 | 5 | 0.134 | 98 | 65 | 26 |

In this series of tests, the main by-product is F123a (CF$_2$Cl—CFClH), which may be recycled into the reactor to form F1123.

EXAMPLE 3

The procedure is as in Example 1B for hydrogenolyzing F1113 with 1.26 of the catalyst of Example 2A.

The following table collates the working conditions for these tests and the results obtained.

| Reactor temp. (°C.) | Mole ratio $H_2$/F1113 | Total flow rate (mole/ hour) | Degree of conversion of F1113 (%) | Selectivity for F1123 (%) |
|---|---|---|---|---|
| 250 | 0.8 | 0.045 | 15 | 98 |
| 300 | 0.8 | 0.045 | 40 | 96 |

EXAMPLE 4

The procedure is as in Example 1B for the hydrogenolysis of F132b ($CF_2Cl$—$CH_2Cl$) with 1.26 ml of the catalyst of Example 1A.

The working conditions and the results obtained are collated in the following table.

| Reactor temp. (°C.) | Mole ratio $H_2$/F132b | Total flow rate (mole/ hour) | Degree of conversion of F132b (%) | Selectivity for $CF_2$=$CH_2$ (%) |
|---|---|---|---|---|
| 250 | 5 | 0.056 | 20 | 99 |
| 270 | 5 | 0.056 | 46 | 99 |
| 300 | 5 | 0.056 | 76 | 98 |

EXAMPLE 5

50 ml of the catalyst described in Example 1A are introduced into an electrically heated Inconel tube 45 cm long and 2.72 cm in internal diameter, and a mixture of hydrogen and F114 is then passed through it at the mole ratios, flow rates and temperatures shown in the following table, the last part of which collates the results obtained.

| Reactor temp. (°C.) | Mole ratio $H_2$/F114 | Total flow rate (mole/ hour) | Degree of conversion of F114 (%) | Selectivity for $C_2F_4$ (%) |
|---|---|---|---|---|
| 250 | 4 | 0.25 | 47 | — |
| 280 | 4 | 0.25 | 70 | — |
| 300 | 4 | 0.25 | 100 | 80 |
| 300 | 2 | 0.15 | 100 | 80 |

EXAMPLE 6

25 ml (13.5 g) of the catalyst described in Example 1A are introduced into the same reactor as in Example 5, and the hydrogenolysis of F113 is performed under atmospheric pressure.

The working conditions and the results obtained are collated in the following table.

| Reactor temp. (°C.) | Mole ratio $H_2$/F113 | Total flow rate (mole/ hour) | Degree of conversion of F113 (%) | Selectivity for | |
|---|---|---|---|---|---|
| | | | | F1113 (%) | F1123 (%) |
| 177 | 1 | 0.7 | 21.5 | 94.3 | 5.6 |
| 177 | 3 | 0.7 | 33 | 91.4 | 8.6 |
| 177 | 5 | 0.7 | 46 | 89.6 | 10.4 |
| 235 | 3 | 0.7 | 92 | 89.7 | 9.7 |
| 289 | 3 | 0.7 | 99 | 84.6 | 14.2 |
| 395 | 3 | 0.7 | 99.7 | 70.2 | 29.6 |

EXAMPLE 7

Example 6 is repeated with 25 ml (13.5 g) of the catalyst described in Example 2A. The following table collates the working conditions and the results obtained.

| Reactor temp. (°C.) | Mole ratio $H_2$/F113 | Total flow rate (mole/ hour) | Degree of conversion of F113 (%) | Selectivity for | |
|---|---|---|---|---|---|
| | | | | F1113 (%) | F1123 (%) |
| 350 | 3 | 0.72 | 100 | 60.5 | 39.2 |
| 350 | 3.1 | 0.31 | 100 | 50.5 | 48.2 |
| 350 | 3 | 0.15 | 100 | 41 | 57 |
| 350 | 3 | 0.08 | 100 | 39.1 | 58.3 |

EXAMPLE 8

A—PREPARATION OF THE CATALYST

A rotary evaporator is charged with 27 g of a CECA active charcoal in the form of extrudates 3 mm in diameter, having a porosity of 0.87 $cm^3$/g and a specific surface area of 1140 $m^2$/g. 100 ml of an aqueous solution containing 3.5 g of palladium chloride and 1.62 g of hydrated cupric chloride ($CuCl_2.2H_2O$) are introduced, water is then evaporated off under reduced pressure (1 kPa) and the residue is dried at 100° C. The latter is then treated at 450° C. for 3 hours under a stream of hydrogen (10 l/h), and a catalyst is thereby obtained, ready for use, containing 7% of palladium and 2% of copper.

B—HYDROGENOLYSIS OF F113

Working in the same reactor as in Example 5, but with 25 ml of this catalyst containing 7% of palladium and 2% of copper, the results collated in the following table were obtained:

| Reactor temp. (°C.) | Mole ratio $H_2$/F113 | Total flow rate (mole/ hour) | Degree of conversion of F113 (%) | Selectivity for | |
|---|---|---|---|---|---|
| | | | | F1113 (%) | F1123 (%) |
| 202 | 3 | 0.33 | 100 | 49.6 | 38 |
| 146 | 3 | 0.32 | 43 | 56.1 | 30 |
| 171 | 3 | 0.33 | 81 | 55.5 | 32 |
| 235 | 3 | 0.33 | 100 | 47.4 | 43.4 |
| 146 | 2 | 0.72 | 19 | 55 | 32.2 |
| 171 | 2 | 0.71 | 48 | 57.7 | 33 |
| 202 | 2 | 0.71 | 78.8 | 61 | 30.3 |
| 225 | 2 | 0.72 | 91 | 57.3 | 34.7 |
| 273 | 2 | 0.72 | 94 | 55.6 | 38.2 |
| 247 | 3 | 0.71 | 99.2 | 56 | 37.4 |
| 204 | 3 | 0.71 | 79 | 56 | 35.6 |
| 346 | 3 | 0.71 | 100 | 52.7 | 45.2 |
| 401 | 3 | 0.71 | 100 | 51.6 | 48.3 |

EXAMPLE 9

The procedure is as in Example 8A, but with the aqueous solution of palladium chloride and cupric chloride replaced by 100 ml of a pyridine solution containing 4.17 g of silver acetate and 0.506 g of palladium acetate.

A catalyst is thereby obtained, ready for use, containing 0.8% of palladium and 9% of silver. Working in the same reactor as in Example 5 with 25 ml of this catalyst, the hydrogenolysis of F113 was performed at atmospheric pressure and the results collated in the following table were obtained.

| Reactor temp. (°C.) | Mole ratio $H_2$/F113 | Total flow rate (mole/hour) | Degree of conversion of F113 (%) | Selectivity for F1113 (%) | Selectivity for F1123 (%) |
|---|---|---|---|---|---|
| 151 | 3.1 | 0.71 | 1.6 | 88 | 2.4 |
| 191 | 3 | 0.72 | 12.2 | 91 | 1 |
| 234 | 3 | 0.71 | 47.6 | 94 | 1.3 |

EXAMPLE 10

The procedure is as in Example 8A, but with the aqueous solution of palladium chloride and cupric chloride replaced by 100 ml of an aqueous solution containing 0.5 g of hydrated ruthenium chloride (Ru content: 41.5%) and 7.3 g of hydrated cupric chloride ($CuCl_2.2H_2O$).

A catalyst is thereby obtained, ready for use, containing 0.7% of ruthenium and 9% of copper. Using 25 ml of this catalyst to effect the hydrogenolysis of F113 at atmospheric pressure in the same reactor as in Example 5, the results collated in the following table were obtained.

| Reactor temp. (°C.) | Mole ratio $H_2$/F113 | Total flow rate (mole/hour) | Degree of conversion of F113 (%) | Selectivity for F1113 (%) | Selectivity for F1123 (%) |
|---|---|---|---|---|---|
| 180 | 3 | 0.7 | 11 | 90 | 9.7 |
| 235 | 3 | 0.7 | 65.5 | 86.5 | 8.3 |
| 259 | 3 | 0.7 | 91 | 88.8 | 10.8 |
| 278 | 3 | 0.7 | 97.5 | 86.2 | 13.3 |

EXAMPLE 11

The procedure is as in Example 8A, but with the aqueous solution of palladium chloride and cupric chloride replaced by 100 ml of an aqueous solution containing 0.65 g of chloroplatinic acid hexahydrate ($H_2PtCl_6.6H_2O$) and 7.25 g of hydrated cupric chloride ($CuCl_2.2H_2O$).

A catalyst is thereby obtained, ready for use, containing 0.8% of platinum and 9% of copper. Using 25 ml of this catalyst to effect the hydrogenolysis of F113 at atmospheric pressure in the same reactor as in Example 5, the results collated in the following table were obtained.

| Reactor temp. (°C.) | Mole ratio $H_2$/F113 | Total flow rate (mole/hour) | Degree of conversion of F113 (%) | Selectivity for F1113 (%) | Selectivity for F1123 (%) |
|---|---|---|---|---|---|
| 180 | 3 | 0.18 | 3 | 98 | 2 |
| 235 | 3 | 0.18 | 23.2 | 98.3 | 1.7 |
| 290 | 3 | 0.17 | 80 | 96.2 | 3 |
| 320 | 3 | 0.18 | 72 | 93 | 5.5 |
| 235 | 3 | 0.08 | 41 | 98 | 1.2 |
| 290 | 3 | 0.08 | 99 | 94 | 4 |
| 260 | 3 | 0.08 | 75 | 97 | 2 |

EXAMPLE 12

A—Preparation of the Catalyst

A rotary evaporator is charged with 26 g of a CECA active charcoal in the form of fragments 2 to 2.5 mm in size, having a porosity of 0.22 $cm^3$/g and a specific surface area of 1000 $m^2$/g. 100 ml of an aqueous solution containing 0.61 g of hydrated rhodium chloride $RhCl_3$ (40.4% of rhodium) and 7.29 g of hydrated cupric chloride ($CuCl_2.2H_2O$) are introduced, the water is then evaporated off under reduced pressure (1 kPa) and the residue is dried at 100° C. The latter is then treated at 450° C. for 3 hours under a stream of hydrogen (10 l/h), and a catalyst is thereby obtained, ready for use, containing 0.85% of rhodium and 9.4% of copper.

B—Hydrogenolysis of F113

Working in the same reactor as in Example 5, but with 25 ml of this catalyst containing 0.85% of rhodium and 9.4% of copper, the results collated in the following table were obtained:

| Reactor temp. (°C.) | Mole ratio $H_2$/F113 | Total flow rate (mole/hour) | Degree of conversion of F113 (%) | Selectivity for F1113 (%) | Selectivity for F1123 (%) |
|---|---|---|---|---|---|
| 180 | 3 | 0.17 | 4 | 70.5 | 29.5 |
| 235 | 3 | 0.17 | 33 | 74 | 24 |
| 290 | 3 | 0.17 | 91.3 | 76.3 | 23 |

EXAMPLE 13 (Comparative)

A—Preparation of the Catalyst

A rotary evaporator is charged with 27 g of a CECA active charcoal in the form of extrudates 3 mm in diameter, having a porosity of 0.87 $cm^3$/g and a specific surface area of 1140 $m^2$/g. 100 ml of an aqueous solution containing 7.3 g of hydrated cupric chloride ($CuCl_2.2H_2O$) are introduced, the water is then evaporated off under reduced pressure (1 kPa) and the residue is dried at 100° C. The latter is then treated at 450° C. for 3 hours under a stream of hydrogen (10 l/h), and a catalyst is thereby obtained, ready for use, containing 9% of copper.

B—Hydrogenolysis of F113

Working in the same reactor as in Example 5, but with 25 ml of this catalyst containing 9% of copper, the results collated in the following table were obtained:

| Reactor temp. (°C) | Mole ratio $H_2/F113$ | Total flow rate (mole/hour) | Degree of conversion of F113 (%) | Selectivity for | |
|---|---|---|---|---|---|
| | | | | F1113 (%) | F1123 (%) |
| 171 | 3 | 0.72 | 0.14 | 79.4 | 20.6 |
| 230 | 3 | 0.71 | 0.95 | 84 | 11.6 |
| 288 | 3 | 0.70 | 3.30 | 97 | 1.4 |
| 340 | 3 | 0.72 | 15.40 | 98 | 1 |

EXAMPLE 14 (Comparative)

A—Preparation of the Catalyst

A rotary evaporator is charged with 23 g of a CECA avtive charcoal in the form of extrudates 1.8 mm in diameter, having a porosity of 0.60 cm³/g and a specific surface area of 947 m²/g. 50 ml of an aqueous solution containing 0.39 g of palladium chloride are introduced, the water is then evaporated off under reduced pressure (1 kPa) and the residue is dried at 100° C. The latter is then treated at 400° C. for 2 hours under a stream of hydrogen (6 l/h), and a catalyst is thereby obtained, ready for use, containing 1% of palladium.

B—Hydrogenolysis of F113

Working in the same reactor as in Example 5, but with 25 ml of this catalyst containing 1% of palladium, the results collated in the following table were obtained:

| Reactor temp. (°C) | Mole ratio $H_2/F113$ | Total flow rate (mole/hour) | Degree of conversion of F113 (%) | Selectivity for | |
|---|---|---|---|---|---|
| | | | | F1113 (%) | F1123 (%) |
| 118 | 3 | 0.70 | 2.8 | 5.5 | 43.8 |
| 223 | 3 | 0.70 | 78.6 | 5.9 | 59 |
| 245 | 3 | 0.68 | 93.6 | 3.8 | 64.8 |

We claim:

1. Process for the manufacture of a fluoroethylene and/or a chlorofluorethylene comprising contacting a mixed catalyst consisting essentially of 1 to 20% by weight of copper and 0.1 to 10% by weight of palladium deposited on an activated carbon support with a chlorofluoroethane of

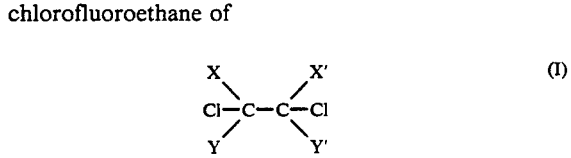

in which at least one of the symbols X, X', Y and Y' represents a fluorine atom and the others, which may be identical or different, each represents a hydrogen or chlorine atom, or with a chlorofluoroethylene of formula:

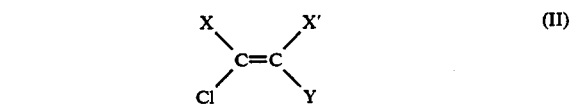

in which at least one of the symbols X, X' and Y represents a fluorine atom and the others, which may be identical or different, each represents a hydrogen or chlorine atom, at a temperature of about 100° to 401° C. with hydrogen to catalytically hydrogenolize the chlorofluoroethane or chlorofluoroethylene of formula (I) or (II) respectively.

2. Process according to claim 1, wherein the hydrogenolysis is performed employing fixed-bed or fluidized-bed operation.

3. Process according to claim 1, wherein the reaction is performed at atmospheric pressure.

4. Process according to claim 1, wherein the mole ratio of hydrogen to the compound (I) or (II) is between 0.1 and 10.

5. Process according to claim 1, wherein the contact time is between 1 and 45 seconds.

6. Process according to claim 1, wherein the copper content is between 3 and 15%.

7. Process according to claim 1, wherein the temperature is between 150° and 350° C.

8. Process according to claim 4 wherein the mole ratio of hydrogen to the compound (I) or (II) is between 0.5 and 5.

9. Process according to claim 5, wherein the contact time is between 2 and 10 seconds.

* * * * *